United States Patent [19]

Kong et al.

[11] Patent Number: 5,200,336
[45] Date of Patent: Apr. 6, 1993

[54] RESTRICTION ENDONUCLEASE OBTAINABLE FOAM BACILLUS COAGULANS AND A PROCESS FOR PRODUCING THE SAME

[75] Inventors: Huimin Kong, Beverly; Ira Schildkraut, Hamilton, both of Mass.

[73] Assignee: New England Biolabs, Inc., Beverly, Mass.

[21] Appl. No.: 547,787

[22] Filed: Jul. 2, 1990

[51] Int. Cl.$^5$ .......................... C12N 9/22; C12N 1/00
[52] U.S. Cl. ..................................... 435/199; 435/832
[58] Field of Search ........................... 435/196; 536/27

[56] References Cited

FOREIGN PATENT DOCUMENTS 0193413 3/1986 European Pat. Off. .
273327 7/1977 Fed. Rep. of Germany .
2930922 7/1979 Fed. Rep. of Germany .

OTHER PUBLICATIONS

Posfai, G. Gene, vol. 69, No. 1, pp. 147–151 (1988).
Brenner, S. Proceedings of the National Academy of Sciences of the USA vol. 86, No. 22, pp. 8902–8906 (1989).
Petrusyte, M. Gene vol., 74, No. 1, pp. 89–91 (1988).
Leung, S. Nucleic Acids Research, vol. 17, No. 23, p. 10133 (1989).
Endow, et al., J. Mol. Biol. 112:521–529 (1977).
Waalwijk, et al., Nucleic Acids Research 5:3231–3236 (1978).
Gingeras, et al., Proc. Natl. Avad. Sci. USA 80:402–406 (1983).
Petrusyte, et al., Dokl. Akad. SSSR 295:1250–1253 (1987).
Kramarov, et al., Bioorg Khim 14:916–920 (1980).
Orekhov, et al., Dokl. Akad. Nauk. SSR 263:217–220 (1982).
Genetic Engineering Principals and Methods, J.K. eds., Plenum Publ. vol. 6 p. 117 (1984).
Lunnen, et al., Gene 74:25–32 (1988).
Brown, et al., J. Mol. Biol. 140:143–148 (1980).
Olson, et al., Science 245:1434–1435 (1989).

Primary Examiner—Elizabeth C. Weimar
Assistant Examiner—Deborah Crouch
Attorney, Agent, or Firm—David G. Conlin; Gregory D. Williams

[57] ABSTRACT

The present invention provides a novel Type II restriction endonuclease obtainable from *Bacillus coagulans*. The endonuclease known as Bcg I, recognizes the following nucleotide sequence and has a cleavage point at both ends outside of its recognition sequence:

5'/(N)10CGA(N)6TGC(N)12/3'
3'/(N)12GCT(N)6ACG(N)10/5' to produce a 34 base pair fragment. Also described is a process for obtaining purified Bcg I from *Bacillus coagulans*, as well as processes for mapping chromosomal DNA and methods for reducing background in transformants with enzymes such as Bcg I.

6 Claims, 3 Drawing Sheets 1 2 3 4 5

1 2 3 4 5 6 7 8 9 10 11 12

AdeMet, or Sinefungin concentration (micromoles)

Km (AdeMet-Bcg I) = 0.1 micromole ●——●
Km (Sinefungin-Bcg I) = 0.5 micromole ×——×

RESTRICTION ENDONUCLEASE OBTAINABLE FOAM BACILLUS COAGULANS AND A PROCESS FOR PRODUCING THE SAME

BACKGROUND OF THE INVENTION

The present invention relates to a novel restriction endonuclease, Bcg I, obtainable from *Bacillus coagulans*, to the process for producing the same, and to related methods of employing this novel enzyme.

Many bacteria contain systems which guard against invasion of foreign DNA. Bacterial cells contain specific endonucleases that make double-strand scissions in invading DNA unless the DNA has been previously modified, usually by the appropriate corresponding DNA methylase. The endonuclease with its accompanying methylase is called a restriction-modification system (hereinafter "R-M system"). The principle function of R-M systems is thus defensive: they enable bacterial cells to resist infections by bacteriophage and plasmid DNA molecules which might otherwise parasitize them.

Bacteria usually possess only a small number of restriction endonucleases per species. The endonucleases are named according to the bacteria from which they are derived. Thus, the species *Haemophilus aegyptius*, for example synthesizes three different restriction endonucleases, named Hae I, Hae II, and Hae III. These enzymes recognize and cleave the sequences (AT)GGCC(AT), PuGCGCPy and GGCC respectively. *Escherichia coli* RY13, on the other hand, synthesizes only one restriction endonuclease, EcoR I, which recognizes the sequence GAATTC.

Restriction endonucleases, the first component of R-M systems, have been characterized primarily with respect to their recognition sequence and cleavage specificity because of their practical use for molecular dissection of DNA. The majority of restriction endonucleases recognize sequences 4–6 nucleotides in length. More recently, recognition endonucleases having recognition sequences of 7–8 nucleotides in length have been found. Most, but not all, recognition sites contain a dyad axis of symmetry, and in most cases, all the bases within the site are uniquely specified. This symmetrical relationship in the recognition sequence of restriction endonucleases has been termed "palindromes". Some restriction endonucleases have degenerate or relaxed specificities in that they can recognize multiple bases at the same positions. Hae III, which recognizes the sequence GGCC is an example of restriction endonuclease having a symmetrical relationship, while Hae II, which recognizes the sequence PuGCGCPy, typifies restriction endonucleases having a degenerate or relaxed specificity. Endonucleases with symmetrical recognition sites generally cleave symmetrically within or adjacent to the recognition site, while those that recognize asymmetric sites tend to cut at distance from the recognition site, typically from about 1–18 base pairs away from the site.

The second component of bacterial R-M system is the modification methylase. These enzymes are complementary to restriction endonucleases and provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the corresponding restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

More than 1,000 different restriction endonucleases have been isolated from bacterial strains, and many share common specificities. Restriction endonucleases which recognize identical sequences are called "isoschizomers". Although the recognition sequences of isoschizomers are the same, they may vary with respect to site of cleavage (e.g., XmaI, SmaI Endow, et al., *J. Mol. Biol.* 112:521 (1977); Waalwijk, et al., *Nucleic Acids Res.* 5:3231 (1978)) and in cleavage rate at various sites (XhoI v. Pae R7I Gingeras, et al., *Proc. Natl. Acad. Sci U.S.A.* 80:402 (1983)).

Three distinct types of R-M systems have been characterized on the basis of the subunit compositions, cofactor requirements, and type of DNA cleavage. Type I R-M systems are the most complex. The endonuclease typically contains three different types of subunits and require $Mg^{++}$, ATP, and S-adenosyl-methionine for DNA cleavage. Their recognition sites are complex, and DNA cleavage occurs at non-specific sites anywhere from 400–7,000 base pairs from the recognition site.

Type II R-M systems are much simpler than either types I or III. The endonuclease only contains one subunit, and only $Mg^{++}$ is required for DNA cleavage. Moreover, the DNA cleavage site occurs within or adjacent to the enzymes' recognition site. It is this class of restriction endonucleases that has proved most useful to molecular biologists.

Type III R-M systems are somewhat less complex than type I systems. The endonuclease of type III R-M systems contain only two types of subunits, and although $Mg^{++}$ and ATP are required for DNA cleavage, S-adenosyl-methionine stimulates enzymatic activity without being an absolute requirement. DNA cleavage occurs distal to the recognition site by about 25–27 base pairs.

Recently, two restriction endonucleases, Gsu I and Eco57 I, were isolated and identified. Both require $Mg^{++}$ and are stimulated by S-adenosyl-methionine (see: Petrusyte et al., Dokl. Akad. Nauk. SSSR 295 p.1250–1253, 1987). These enzymes appear to be a new type of restriction endonuclease. Furthermore, Kramarov, et al. Bioorg. Khim 14 p.916–920, 1980, reported site specific endonuclease BST 4.4I from Bacillus stearothermophilus which was reported to produce two double strand cuts separated with 30 to 32 nucleotides in the region of the recognition site. Additionally, Orekhov et al., Dokl. Akad. Nauk. SSSR 263 p.217–220, 1982 reported Sgr II, an isoschizomer of EcoRI I from Streptomyces griseus, and suggests that it cleaves on both sides of its recognition site.

While a large number of restriction endonucleases are already known for numerous DNA sequences, there is a continuing need for restriction enzymes with diversified enzymatic characteristics for successful genetic manipulation.

SUMMARY OF THE INVENTION

In accordance with the present invention, there is provided a novel type restriction endonuclease obtainable from the bacterium *Bacillus coagulans*, hereinafter referred to as "Bcg I", which endonuclease:

(1) recognizes the DNA sequence:

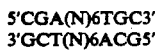

5'CGA(N)6TGC3'
3'GCT(N)6ACG5'

(wherein A, T, C and G represent thymine, cytosine and guanine, respectively);

(2) cleaves at both ends of double-stranded DNA outside of its recognition sequence to produce a 34 base pair ("bp") fragment containing the Bcg I recognition sequence; and (3) cleaves double-stranded phiX174 twice, which was mapped to position 950 and 5,300 according to Bcg I double digestion with Pst I, Nci I and Stu I, and cleaves pUC19 once, which was mapped to position 2,200 with Sca I, Pst I and AlwN I.

The present invention further relates to a process for the production of the novel restriction endonuclease Bcg I which comprises culturing *Bacillus coagulans* under conditions suitable for expressing Bcg I, collecting the cells, obtaining a cell-free extract therefrom and separating and collecting the restriction endonuclease Bcg I from the cell-free extract.

The present invention also relates to a novel method of mapping chromosomal DNA using enzymes such as Bcg I as well as to methods of reducing the background in transformants by inserting the target DNA into the recognition sequence of restriction endonucleases such as Bcg I and subjecting its library to restriction by an appropriate enzyme.

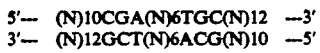

5'— (N)10CGA(N)6TGC(N)12 —3'
3'— (N)12GCT(N)6ACG(N)10 —5'

Figure 4:
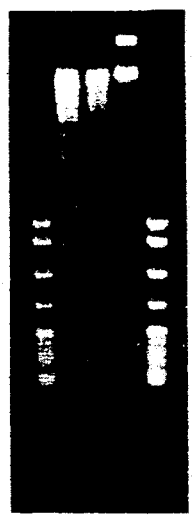

FIG. 4 is an agarose gel confirming that digestion with Bcg I produces a 34 base pair fragment. Lane 1: pBR322+Msp I, size standard; Lane 2: lambda+Bcg I; Lane 3: lambda+Bcg I without MG++; Lane 4: lambda+Bcg I, without AdoMet; and Lane 5: lambda+HindIII, Phix174+HaeIII, size standard.

Figure 5:
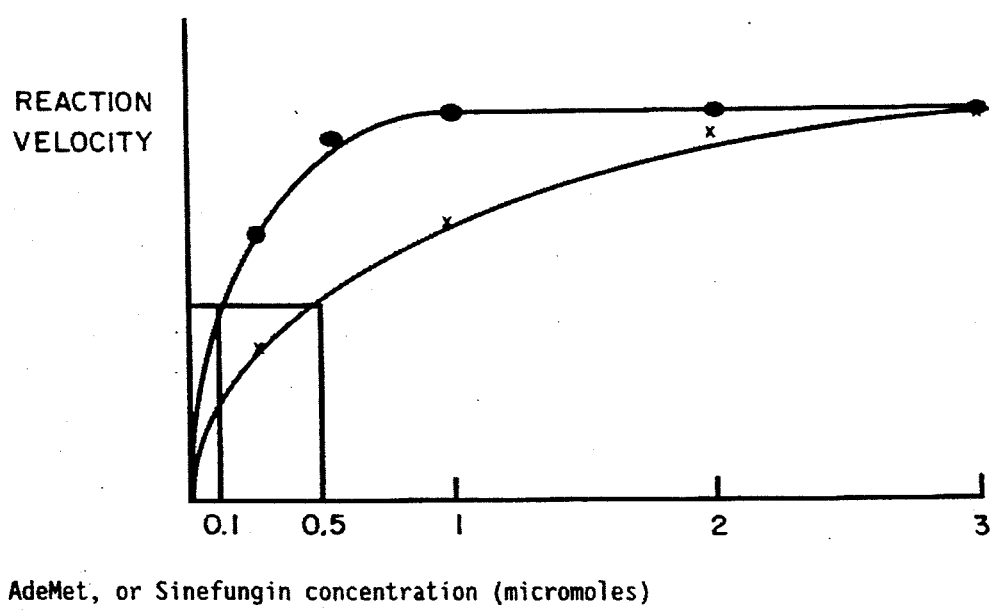

FIG. 5 illustrates the rate of Bcg I cleavage at varying concentrations of S-adenosyl methionine and Sinefungin illustrating the Km of Bcg I with AdeMet and Sinefungin using 1×Bcg I to digest 1 ug lambda DNA at 30° C. for 15 minutes. (AdeMet=S-adenosylmethionine).

DETAILED DESCRIPTION OF THE INVENTION

In accordance with the present invention, Bcg I is obtained by culturing *Bacillus coagulans* strain NEB Strain No. 566 and recovering the enzyme from the cells. A sample of *Bacillus coagulans* was deposited with the American Type Culture Collection (ATCC) on May 31, 1990, and bears ATCC Accession No.55055.

Bacillus coagulans strain NEB 566 was isolated from soil and plated on LB agar. Selected colonies were picked and plate purified. Purified samples were assayed for endonuclease activity in accordance with the technique described by Schildkraut in *Genetic Engineering Principles and Methods*, (1984) Setlow, J. K. et al., eds., Plenum Publishing, Vol. 6, pg. 117, the disclosure of which is hereby incorporated by reference. One sample identified as Bacillus coagulans NEB 566 contained the novel restriction endonuclease Bcg I.

For recovering the enzyme of the present invention, *Bacillus coagulans* may be grown using any suitable technique. For example, *Bacillus coagulans* may be grown in Luria Broth (LB) medium (pH 7.2) at 37° C. with agitation and aeration. Cells in the late logarithmic stage are collected using centrifugation and stored frozen at −70° C.

After the cells are harvested and frozen, the enzyme can be isolated and purified from the frozen cell paste by using conventional enzyme purification methods. For example, the obtained cell paste is thawed and suspended in a buffer solution and subjected to treatment to allow extraction of the enzyme by the buffer solution, such treatment includes sonication, high pressure dispersion, or enzymatic digestion. The cell residue is then removed by centrifugation, and the supernatant containing the new enzyme can be purified by ion-exchange chromatography, using for example phosphocellulose or DEAE-cellulose, molecular sieve chromatography and affinity chromatography, using for example heparin agarose or DNA-cellulose, or a combination of these methods, to produce the enzyme of the present invention.

Figure 1:
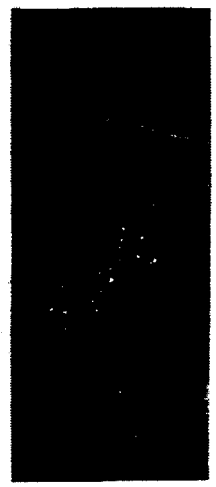
FIG. 1 illustrates the results of an assay demonstrating the cofactor requirements for Bcg I. Assay of the cofactors which are required in Bcg I digestion are as follows: lane 1: Bcg I digest of T7 DNA with ATP, AdeMet, and Mg. Lane 2: Bcg I digest of T7 DNA without ATP. Lane 3: Bcg I digest of T7 DNA without AdeMet. Lane 4: Bcg I digest of T7 DNA without Mg. Lane 5: Hind III—lambda DNA and Hae III.

As discussed below in Example 1, it was found that the crude extract, as well as the protein obtained after one column, did not require the presence of S-adenosyl methionine, but as the Bcg I became more pure, the endonuclease activity of Bcg I was completely dependent on the presence of S-adenosyl methionine as a cofactor (see FIG. 1). Sinefungin (obtained from Cal Biochem), a structural analogue of S-adenosyl methionine also acts as a cofactor, indicating that Bcg I does not require the transfer of the methyl group of S-adenosyl methionine and therefore cleavage is not dependent on methylation of the recognition sequence.

The restriction endonuclease of the present invention along with its corresponding DNA methylase may also be obtained using recombinant DNA techniques, such as the methylase selection technique disclosed by Wilson, et al., EPO Publication No. 019413, the disclosure of which is herein incorporated by reference. The methylase selection technique can be carried out in three steps. First, DNA from a bacterial strain encoding the R-M system is purified, partially digested with cloning endonucleases, and then ligated to a cleaved, dephosphorylated plasmid vector. The ligated DNA is transformed into E. coli, the transformants are pooled and the populations of plasmids are purified to form libraries. Next, the libraries are digested with a selecting endonuclease, one which can be blocked by the specific modification that the methylase confers. The digests are transformed back into E. coli to recover undigested molecules. The transformants can be screened immediately, or pooled and the plasmids cycled through further rounds of purification and selection. Finally, individual transformants are collected and mini-preparations are made of their plasmids. The plasmids are analyzed for resistance to digestion by the endonuclease of interest and for possession of common inserts. (The methylase gene will be encoded by at least one fragment, which will generally be present in all bona fide methylase clones.) Cell extracts are prepared from positive candidates and assayed in vitro for methyltransferase activity and endonuclease activity.

A number of R-M systems, however, have been found to be more complex and therefore more difficult to obtain using standard recombinant DNA techniques such as the above-described methylase selection approach, and may require modification for successful cloning of R-M systems, (see Lunnen, et al., (1988) Gene 74:25–32, the disclosure of which is hereby incorporated by reference). For example, in some systems, the methylase and endonuclease genes may not be linked or the endonuclease used to fragment the bacterial DNA may cut either or both of the R-M genes. In other systems, such as BamHI and DdeI, the methylase may not protect sufficiently against digestion by the corresponding endonuclease, either because of the inefficient expression in the transformation host, or because of the inherent control mechanism for expression of the methylase and endonuclease genes, or for unknown reasons. Modification has also been found to be harmful to the host cell chosen for transformation. Another difficulty in cloning R-M systems is that the endonuclease sought to be cloned may not be available in sufficient purity or quantity for methylase selection. Finally, in many systems, difficulties are encountered in expressing the endonuclease gene in a transformation host cell of a different bacterial species.

The recognition sequence of the endonuclease of the present invention, Bcg I can be determined by double-digesting phix174, pUC19 and T7 DNA with the restriction endonuclease of the present invention and a restriction enzyme which cleaves test DNA at known sites. The size of the DNA restriction fragments obtained can be determined using agarose gel electrophoresis. Using this technique, the following results illustrated in FIG. 2 were obtained:

(a) The two recognition sequences of Bcg I on phix174 DNA were mapped to approximately 950 and 5,300 base pairs by analysis against Pst I, Nci I and Stu I cleaved phix174 DNA. The sequence 5'CGA(N)6TGC3' occurs twice at positions 967 and 5,362 base pairs.

(b) The single recognition sequence of Bcg I on pUC19 was mapped to approximately 2,200 base pairs by analysis against Sca I, Pst I and AlwN I cleaved pUC19 DNA. The sequence 5'CGA(N)6TGC3' occurs at only one position 2,215 base pairs.

Figure 2:
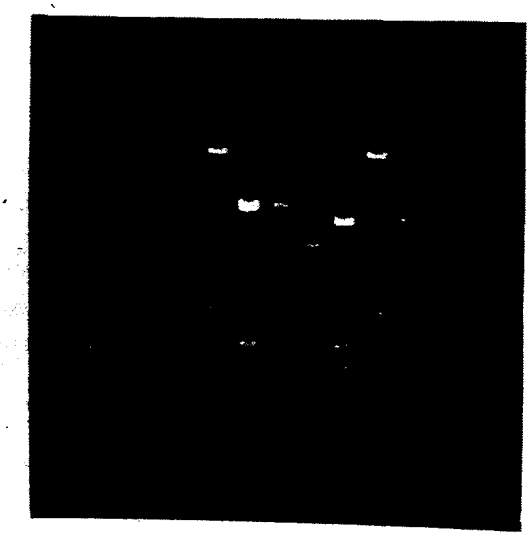
FIG. 2 is a gel used to determine the recognition sequence of Bcg I. Identification of Bcg I recognition sequence is as follows: Lane 1: pUC19+Bcg I. Lane 2: 1+SCA I. Lane 3: 1+AlwN I. Lane 4: 1+Pst I. Lane 6: phix174+Bcg I. Lane 7: 6+Pst I. Lane 8: 6+Nci I. Lane 9: 6+Stu I. Lane 11: lambda+Bcg I. Lane 12: T7+Bcg I. Lane 5 and 10: lambda+Hind III and phix174+Hae III, size standard.

(c) The predicted fragment sizes generated by cleavage of lambda and T7 DNA based on the number of Bcg I recognition sites known to exist in these DNAs matched the observed fragment sizes from Bcg I digests of these DNAs (see FIG. 2, lanes 11 and 12).

As is shown in Table 1, the number of the fragments generated by digestion with Bcg I on six DNA molecules match the computer predicted number of the fragments that would be generated by cleavage at the sequence 5'CGA(N)6TGC3', and the location of the cleavage sequence for 6 mapped sequences match the computer predicted location.

From the above data, it was thus concluded that Bcg I recognizes the sequence 5'CGA(N)6TGC3'.

The point of cleavage on the recognition sequence of the endonuclease of the present invention can be determined by using the method described in Brown et al., J. Mol. Biol. 140 p.143–148, 1980.

Figure 3:
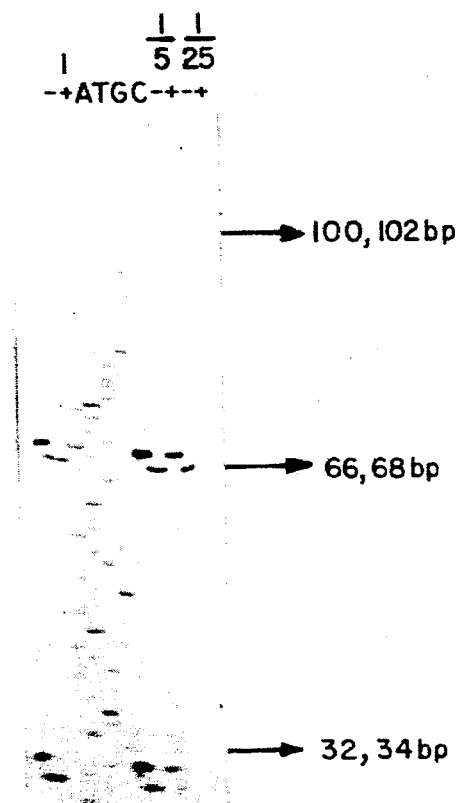
FIGS. 3 and 3A are a sequencing gel and illustration demonstrating that Bcg I cuts on both sides of its recognition sequence to produce a 34 base pair fragment. ⊕indicates addition of Klenow fragment subsequent to Bcg I digestion. ⊖no Klenow added. The cleavage site of Bcg I is.
Figure 3A:
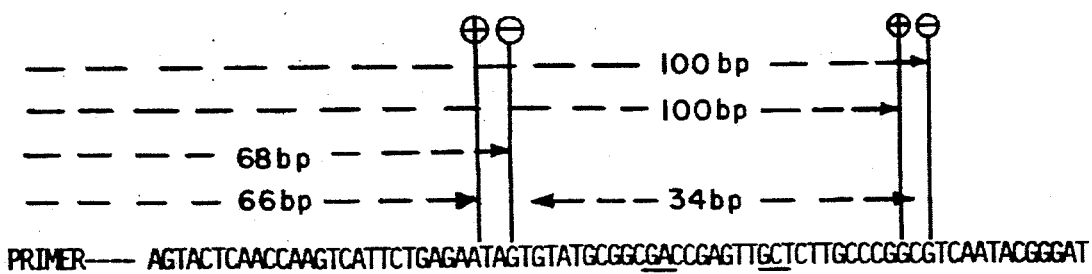

Briefly, pUC19 was used as the template and an appropriate primer (2138–2155) upstream of the 2215 Bcg I site was used for the extension and dideoxy sequencing reaction. Bcg I cleaves twice at both sides of its recognition sequence to generate a 34 bp fragment with a 2 base 3' extensions (FIG. 3). The sequencing data on pBR322 confirmed this result. There are also 29 Bcg I recognition sites on lambda DNA. The 34 base pair fragments of Bcg I digest of lambda DNA appeared at the bottom of an agarose gel (FIG. 4) as is expected if Bcg I cuts on both sides of its recognition sequence to produce twentynine 34 bp fragments.

TABLE 1

| a) Number of BcgI recognition sites on lambda, T7 and Adeno2 DNA. | | |
|---|---|---|
| | computer generated number of cleavage sites | observed no. of fragments |
| lambda | 28 | >24 |
| T7 | 19 | >16 |
| Adeno2 | 10 | >9 |

| b) Location of BcgI recognition sequences in pBR322, pUC19, and PhiX174 DNA. | | |
|---|---|---|
| | computer generated positions | positions mapped by double digestion |
| pBR322 | 707,2064,3883 | 700,2100,3900 |
| PhiX174 | 967,5362 | 950,5300 |
| pUC19 | 2215 | 2200 |

Using the techniques described above it was concluded that Bcg I cleaves both strands of DNA on each side of its recognition sequence:

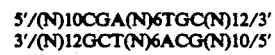

to produce a 34 bp fragment.

The enzyme of the present invention has the following additional properties:

(a) The Km for S-adenosyl methionine and Sinefungin is illustrated in FIG. 5. The concentration of lambda DNA and enzymes were kept constant, while the concentrations of S-adenosyl methionine and Sinefungin were changed from 0.01 μM to 10 μM. The Km of S-adenosyl methionine-Bcg I is about 0.1 μM while the Km of Sinefungin-Bcg I is about 0.5 μM.

(b) The optimal digestion condition is : 100 mM NaCl, 10 mM Tris-HCl (pH 8.4), 10 mM MgCl$_2$, 10 mM 2-mercaptoethanol, 20 μM S-adenosyl methionine at 37° C.

(c) Temperature: Bcg I is stable over a temperature range of about 25° C. to 37° C. Temperature stability was determined by incubating 1 unit of Bcg I (defined as the amount of enzyme required to completely digest 1 ug lambda DNA at 30° C. in 60 minutes in 50 ul reaction volume) in its optimal condition without one of the following: Mg$^{++}$, or S-adenosyl methionine, or DNA at 25, 37 and 55 degrees. After incubating for 30 minutes, Bcg I activity was assayed at 30° C. by adding the third component (Mg$^{++}$, S-adenosyl methionine, or DNA). At 25° and 37° the enzyme did not lose activity but at 55° Bcg I lost activity under all three conditions.

In accordance with another embodiment of the present invention, there is provided a method of mapping DNA comprising a) forming a recombinant DNA library from the base pair DNA fragments that result from digesting the DNA with an enzyme which cleaves its recognition sequence from the DNA (such as Bcg I), b) separating individual clones which each contain a single unique base pair insert, and c) use of these clones as DNA probes for the target DNA. Such probes would contain sufficiently unique DNA to allow identification of large regions of DNA from which they originated. This approach to mapping using, e.g., 32 base pair insert libraries generated by Bcg I, would be analogous to the proposed sequence tagged sites (STS's) disclosed in M. Olson et al., Science 245:1434 (1989), the disclosure of which is incorporated by reference herein. Using Bcg I, the individual cloned 32 base pair fragments would uniquely id.:ntify (tag) a larger region of DNA. In addition to unique tagging of larger stretches of DNA, overlaps of two larger DNA fragments could be readily established. This mapping technique would be particularly useful in mapping chromosomal DNA such as human chromosomal DNA.

In yet another embodiment, there is provided a method of reducing the background DNA in transformants comprising a) inserting a first predetermined recognition site into a second predetermined recognition site of a vector containing said second recognition site, wherein the second predetermined recognition site's recognition sequence is interrupted by one or more unspecified nucleotides;

b) ligating a target DNA into said first recognition sequence of said vector to form a library for a transformation reaction;

c) contacting the library of step b with a restriction endonuclease which restricts DNA containing said second predetermined recognition site; and d) transforming a host cell with the resulting library of step c.

For example, a vector can be readily constructed containing a Bcg I site wherein the internal six nucleotides are GAATTC (the recognition sequence of EcorI), or CATATG (which is part of the recognition sequence of Nde I). These internally created sites can then be used in a conventional manner, e.g., for inserting and ligating a target DNA. Exposing the product of the ligation reaction to Bcg I would effectively lower the background for the subsequent transformation reaction since only vectors containing a target DNA inserted within the Bcg I site would survive Bcg I restriction. Those vectors which do not have an inserted DNA would be cleaved by Bcg I and therefor, not transform the host. In other words, only vectors containing insert DNA within the Bcg I recognition site would transform with high efficiency.

The following examples are given to illustrate embodiments of the present invention as it is presently preferred to practice. It will be understood that the examples are illustrative, and that the invention is not to be considered as restricted except as indicated in the appended claims.

EXAMPLE I

Purification of Bcg I

All steps were performed at 4° C.

Step 1: Preparation of Crude Extract.

Bcg I was isolated from Bacillus coagulans NEB 566 grown at 37 degrees C with aeration in the media (tryptone 10 g per liter, yeast extract 5 g per liter, NaCl 5 g per liter, 1 mM MgCl2, pH adjusted to pH 7.2). The cells were harvested by centrifugation. 400 grams of cell paste were suspended in 900 ml P Buffer (50 mMNaCl, 10 mM potassium phosphate pH 6.5, 10 mM 2-mercaptoethanol, 0.1 mM EDTA, 10% glycerol). The cells were ruptured by sonicating for 10 minutes. The extract was centrifuged in a Beckmann J2-2P centrifuge at 4° C. at 30K for 30 minutes. The supernatant fluid was decanted.

Step 2: Phosphocellulose Chromatography.

The supernatant fluid from step 1 was applied to a 5×16 cm phosphocellulose column (Whatman P11) which had been equilibrated with P buffer. The column was washed with 300 ml P buffer and then enzyme was eluted with a 3,000 ml linear gradient (0 to 1M NaCl) in P buffer. The fractions were assayed for Bcg I activity and the active fractions were pooled.

Step 3: Hydroxylapatite Chromatography.

The pool. from the previous step was applied directly to a 2.5×10 cm Hydroxylapatite column. The enzyme was eluted with a 500 ml linear gradient (10 mM to 700 mM potassium phosphate pH 7.0) in 0.5M Nacl, 10 mM 2-mercaptoethanol, 0.1 mM EDTA. The fractions were assayed for Bcg I activity and the active fractions were pooled.

Step 4: Heparin Sepharose Chromatography.

The pool from the previous step was dialyzed twice against H buffer (10 mM Tris-HCl pH 7.4, 50 mM NaCl, 10 mM 2-mercaptoethanol, 0.1 mM EDTA), and applied to a heparin sepharose (Pharmacia) column (1×10 cm) which had been equilibrated with H buffer. The enzyme was eluted with a 100 ml linear gradient (50 mM to 1M NaCl) in H buffer. The fractions were assayed for Bcg I activity and the active fractions were pooled. The pool was dialyzed against storage buffer (50 mM KCl, 10 mM Tris-HCl (pH 7.4), 0.1 mM EDTA, 10 mM 2-mercaptoethanol, and 50% glycerol). The enzyme is preferably stored at −20° C. The enzyme preparation was substantially pure and free from other contaminating enzymes/proteins and contained no detectable non-specific nuclease activity as determined by incubating one unit of enzyme in a 100 μl reaction in optimal reaction conditions for 16 hours. The resulting DNA gel banding pattern was identical to the same reaction incubated for one hour.

EXAMPLE II

Mapping Chromosomal DNA with Bcg I

Chromosomal DNA is digested completion with Bcg I. The DNA fragments are then separated according to size by a method such as agarose gel electrophoresis. The band on the gel corresponding to the 34 base pair DNA fragments is then collected. The collection of the 34 base pair DNA fragments are treated with a DNA polymerase such as E.coli DNA polymerase Klenow fragment and all four deoxynucleotide triphosphates (dATP, dTTP, dGTP, dCTP) to remove the 3' 2-base extensions. The resulting 32 base pair DNA fragments are then ligated into a DNA vector such as pUC19 at a cleaved blunt ended restriction site such as Sma I. The collection of ligated DNA molecules is then used to transform E. coli to form a recombinant library of 32 base pair insert DNA. This library would contain clones which contain unique DNA which hybridize specifically to unique positions in chromosomal DNA. The individual clones then represent unique tags for much larger DNA fragments such as found in lambda libraries, YAC libraries, cosmid libraries and restriction endonuclease digests of chromosomal DNA.

What is claimed is:

1. A restriction endonuclease obtainable from *Bacillus coagulans*, ATCC No. 55055, where said endonuclease recognizes the following base sequence in double-stranded deoxyribonucleic acid molecules:

5'... ↓(N)10CGA(N)6TGC(N)12↓ ...3'
   3'... ↑(N)12GCT(N)6ACG(N)10↑ ...5' and cleaves said deoxyribonucleic acid molecules at both ends of the recognition sequence as indicated by the arrows.

2. The restriction endonuclease of claim 1, having a greater stability between 25° C. and 37° C. than at 55° C.

3. The restriction endonuclease of claim 1, cleaving double-stranded deoxyribonucleic acid phix174 at two positions and pUC19 at one position.

4. The restriction endonuclease of claim 1, wherein the restriction endonuclease is purified from *Bacillus coagulans* (ATCC No. 55055).

5. A method for obtaining the restriction endonuclease of claim 1, comprising cultivating a sample of *Bacillus coagulans* obtainable from ATCC No. 55055 under conditions favoring production of said endonuclease and separating said endonuclease therefrom.

6. A composition comprised of a restriction endonuclease obtainable from *Bacillus coagulans*, ATTC No. 55055, where said endonuclease recognizes the following base sequence in double-stranded deoxyribonucleic acid molecules:

5'... ↓(N)10CGA(N)6TGC(N)12↓ ...3'
   3'... ↑(N)12GCT(N)6ACG(N)10↑ ...5' and cleaves said deoxyribonucleic acid molecules at both ends of the recognition sequence as indicated by the arrows and a co-factor selected from the group S-adenosyl-methionine or analogs thereof.

* * * * *